United States Patent
Kikuchi (10) Patent No.: US 9,841,591 B2
(45) Date of Patent: Dec. 12, 2017

(54) MICROSCOPE SWITCHABLE BETWEEN BRIGHT-FIELD OBSERVATION AND FLUORESCENCE OBSERVATION HAVING MOVABLE LENS

(71) Applicant: OLYMPUS CORPORATION, Shibuya-ku, Tokyo (JP)

(72) Inventor: Yu Kikuchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 333 days.

(21) Appl. No.: 14/546,910

(22) Filed: Nov. 18, 2014

(65) Prior Publication Data
US 2015/0198796 A1    Jul. 16, 2015

(30) Foreign Application Priority Data

Jan. 14, 2014  (JP) .................................. 2014-004521

(51) Int. Cl.
*G02B 21/00*     (2006.01)
*G02B 21/12*     (2006.01)
(Continued)

(52) U.S. Cl.
CPC .......... *G02B 21/0076* (2013.01); *G02B 21/12* (2013.01); *G02B 21/16* (2013.01);
(Continued)

(58) Field of Classification Search
CPC ............. G01N 21/645; G01N 21/6456; G01N 21/6458; G02B 7/14; G02B 7/16;
(Continued)

(56) References Cited

U.S. PATENT DOCUMENTS

2001/0008461 A1*  7/2001  Koyama .................. G02B 7/16
                                                                359/380
2003/0016301 A1    1/2003  Aizaki et al.
(Continued)

FOREIGN PATENT DOCUMENTS

JP        10142507 A    5/1998
JP        11037053 A    2/1999
(Continued)

OTHER PUBLICATIONS

Extended European Search Report dated Jul. 13, 2015, issued in counterpart European Application No. 14193469.5.
(Continued)

*Primary Examiner* — Stephone B Allen
*Assistant Examiner* — Ryan S Dunning
(74) *Attorney, Agent, or Firm* — Holtz, Holtz & Volek PC (57) ABSTRACT

A microscope is a microscope that switches an observation method between the bright-field observation and the fluorescence observation. The microscope includes an objective that irradiates a sample with excitation light and converts fluorescence from the sample into a parallel light flux, a beam splitter that splits fluorescence and excitation light from each other, and a collective lens that is arranged in such a manner that it is freely set in and removed from an optical path between the beam splitter and the objective, that has a positive power, and that is set in the optical path for fluorescence observation and is removed from the optical path for bright-field observation.

7 Claims, 6 Drawing Sheets

(51) Int. Cl.
*G02B 21/16* (2006.01)
*G01N 21/64* (2006.01)
*G02B 7/16* (2006.01)
*G02B 21/24* (2006.01)
*G02B 27/10* (2006.01)
*G02B 27/14* (2006.01)

(52) U.S. Cl.
CPC ....... *G01N 21/645* (2013.01); *G01N 21/6456* (2013.01); *G01N 21/6458* (2013.01); *G02B 7/16* (2013.01); *G02B 21/248* (2013.01); *G02B 27/1006* (2013.01); *G02B 27/141* (2013.01)

(58) Field of Classification Search
CPC .............. G02B 21/002; G02B 21/0024; G02B 21/0032; G02B 21/04; G02B 21/0076; G02B 21/12; G02B 21/16; G02B 21/248; G02B 2207/113; G02B 2207/114; G06T 2207/10056; G06T 2207/10064; G06T 2207/10121
USPC ..... 348/79, 80; 356/904; 359/368, 381, 384, 359/385, 388, 389, 656; 378/43, 44
See application file for complete search history.

(56) References Cited

U.S. PATENT DOCUMENTS

| | | | |
|---|---|---|---|
| 2006/0238858 A1 | 10/2006 | Kawasaki et al. | |
| 2007/0121473 A1 | 5/2007 | Lange et al. | |
| 2008/0030849 A1* | 2/2008 | Fukuyama | G02B 21/0012 359/381 |
| 2008/0158566 A1 | 7/2008 | Suzuki et al. | |
| 2010/0268042 A1* | 10/2010 | Wang | A61B 5/0059 600/322 |

FOREIGN PATENT DOCUMENTS

| | | |
|---|---|---|
| JP | 2005115273 A | 4/2005 |
| JP | 2006301599 A | 11/2006 |
| JP | 2007510176 A | 4/2007 |
| JP | 2008175884 A | 7/2008 |
| JP | 2008225096 A | 9/2008 |

OTHER PUBLICATIONS

Japanese Office Action (and English translation thereof) dated Aug. 8, 2017 issued in counterpart Japanese Application No. 2014-004521.

* cited by examiner

<PRIOR ART>

MICROSCOPE SWITCHABLE BETWEEN BRIGHT-FIELD OBSERVATION AND FLUORESCENCE OBSERVATION HAVING MOVABLE LENS

CROSS REFERENCE TO RELATED APPLICATIONS

This application is based upon and claims the benefit of priority from prior Japanese Patent Application No. 2014-004521, filed Jan. 14, 2014, the entire contents of which are incorporated herein by this reference.

BACKGROUND OF THE INVENTION

Field of the Invention

The present invention is related to a microscope and particularly to a microscope that splits the illumination optical path and the detection optical path from each other by using a dichroic mirror.

Description of the Related Art

Figure 1:
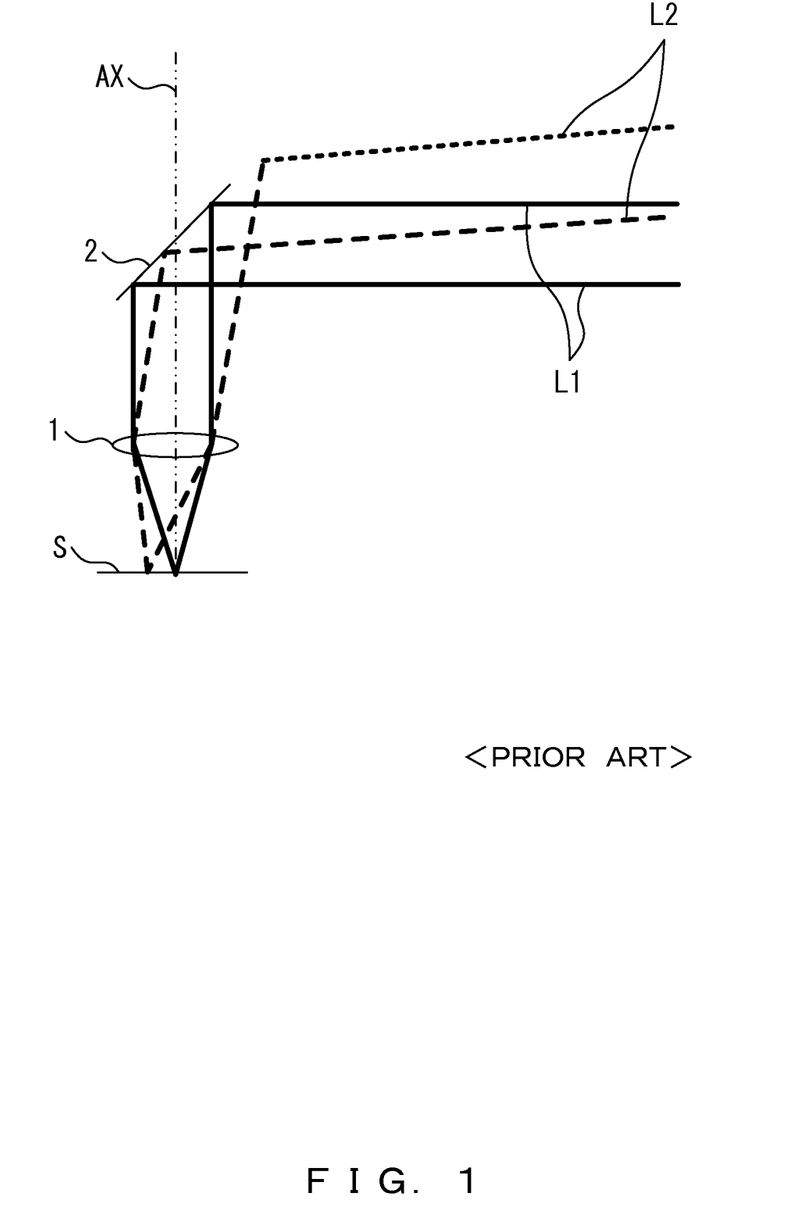
FIG. 1 shows on-axis light and off-axis light emitted from the objective to the dichroic mirror in a conventional fluorescence microscope.

A fluorescence microscope employing epi-illumination generally has a dichroic mirror for splitting the illumination light and the detection light from each other in the optical path between the objective and the photodetector. It is known that fluorescence that has been converted by the objective into a parallel light flux is incident on this dichroic mirror and off-axis light of the fluorescence is often subject to vignetting at the dichroic mirror. This is because on-axis light L1 is emitted from the pupil of an objective 1 in the direction parallel to optical axis AX whereas off-axis light L2 is emitted from the pupil of the objective 1 at an angle from optical axis AX (referred to as an emission angle at the pupil position or as an emission angle hereinafter) as shown in FIG. 1. The emission angle at the pupil position becomes greater with an increasing distance between the position of the generation of the fluorescence (off-axis light L2) and optical axis AX, and accordingly fluorescence generated at a position that is far away from optical axis AX misses a dichroic mirror 2, resulting in vignetting at the dichroic mirror 2. In reality, the upper off-axis light L2 in FIG. 1 is not reflected by the dichroic mirror 2 and is blocked by the frame etc., however, it is assumed that there is a mirror and the light is depicted by a different type of line.

As described above, conventional microscopes are subject to a limitation of a scope which is located on a sample surface and from which is emitted fluorescence that can be captured (referred to as a capturing field of view hereinafter) in accordance with the diameter of a dichroic mirror, and accordingly there are cases where the capturing field of view of a microscope does not match the maximum capturing field of view which can be supported by an objective, making it impossible to fully utilize the performance capability of the objective.

In order to solve the above described technical problem, for example an arrangement might be conceivable in which the dichroic mirror is set close to the objective so that off-axis light will not miss the dichroic mirror. However, there is a structure, such as a revolver etc., between the dichroic mirror and the objective, imposing limitations on the reduction in the distance between the dichroic mirror and the objective.

Note that the Japanese National Publication of International Patent Application No. 2007-510176 discloses a scanning laser microscope including an additional optical system, for reducing the light flux diameter of detected light, located between a beam splitter for splitting the excitation light and the detection light from each other and an optical system for delivering the detection light to a detector. The additional optical system disclosed by the Japanese National Publication of International Patent Application No. 2007-510176 is for realizing the formation of as large a field of view as possible in the detector.

SUMMARY OF THE INVENTION

One aspect of the present invention provides a microscope that switches the observation methods between the bright-field observation and the fluorescence observation, the microscope including an objective that irradiates a sample with excitation light and converts fluorescence from the sample into a parallel light flux, a beam splitter that splits fluorescence and excitation light from each other, and a collective lens that is arranged in such a manner that the collective lens is freely set in and removed from an optical path between the beam splitter and the objective, that has a positive power, and that is set in the optical path for the fluorescence observation and is removed from the optical path for the bright-field observation.

BRIEF DESCRIPTION OF THE DRAWINGS

The present invention will be more apparent from the following detailed description when the accompanying drawings are referenced.

DESCRIPTION OF THE EMBODIMENTS

Embodiment 1

Figure 2:
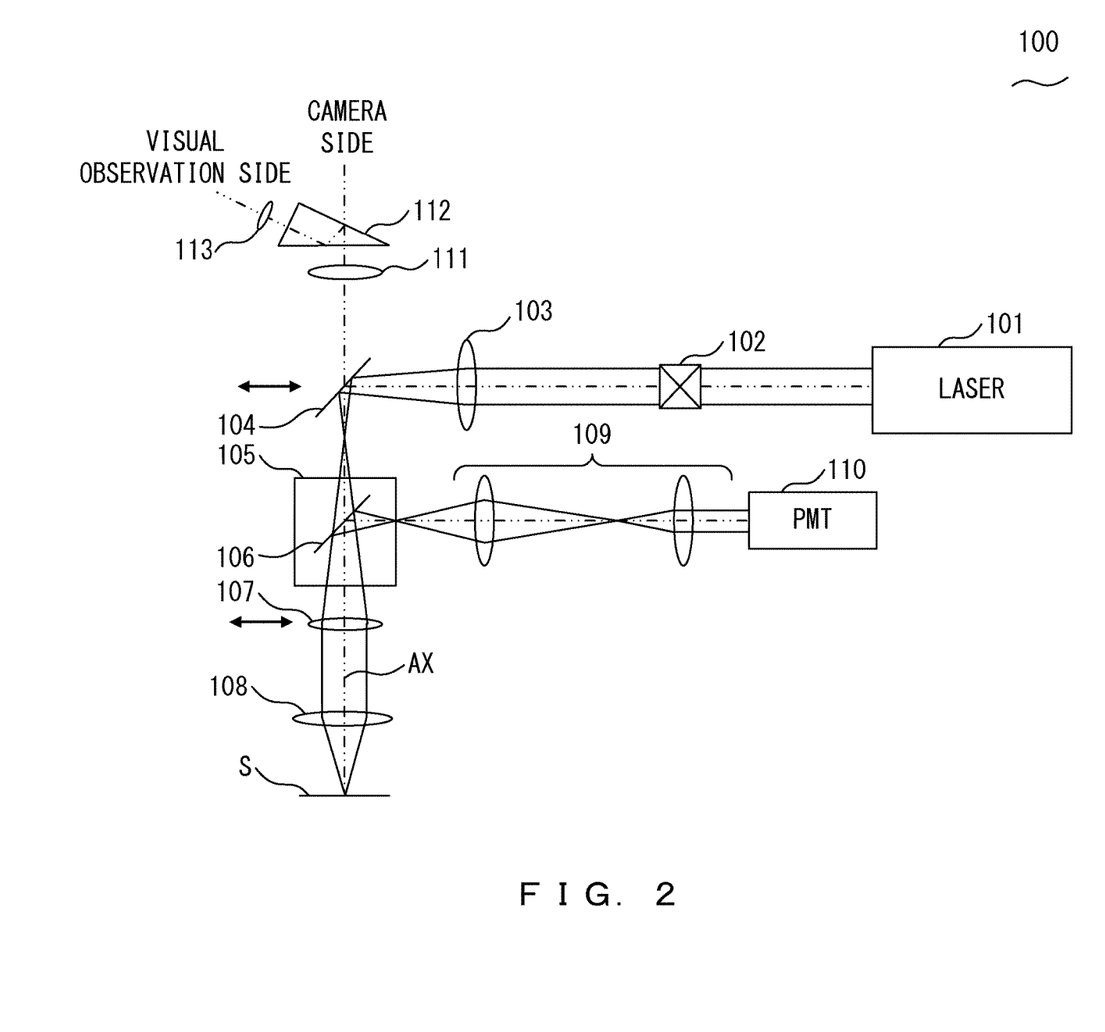
FIG. 2 exemplifies a configuration of a microscope according to embodiment 1 of the present invention.

FIG. 2 exemplifies a configuration of a microscope 100 according to the present embodiment. The microscope 100 is a microscope that switches the observation methods between the bright-field observation and the fluorescence observation.

As shown in FIG. 2, the microscope 100 includes a galvano mirror 102 at a position (pupil conjugate position) optically conjugate with the position of the pupil of an objective 108 disposed in the laser optical path, and also includes a PMT 110 as a non-De scanned detector (NDD) at a pupil conjugate position of the objective 108 disposed in the fluorescence detection optical path. The microscope 100, employing this configuration, functions as a two-photon excitation microscope for conducting the fluorescence observation. Also, a two-photon excitation microscope is a type of non-linear optical microscope, and causes two-photon absorption at sample S through irradiation with laser light, which is used as the excitation light, so as to detect fluorescence generated in the two-photon absorption process.

Hereinafter, more detailed explanations will be given for a configuration of the microscope 100. The microscope 100 includes a laser 101 that emits laser light, which serves as excitation light. The microscope 100 includes, on the illumination optical path (laser optical path), the galvano mirror 102, a pupil projection lens 103, a mirror 104, a fluorescence cube 105 having a dichroic mirror 106 therein, a collective lens 107, and the objective 108.

The laser 101 is for example a titanium-sapphire laser that emits high-power laser light having a pulse width on the order of femtoseconds or picoseconds. The galvano mirror 102 is a scanner that scans sample S with laser light by deflecting laser light from the laser 101, and is arranged at the pupil conjugate position of the objective 108.

The pupil projection lens 103 constitutes, together with the collective lens 107, a pupil relay optical system that projects the pupil of the objective 108 onto the galvano mirror 102. The mirror 104 is a mirror that reflects laser light toward the objective 108. The mirror 104 is arranged in such a manner that it is freely set in and removed from the optical path of laser light, and is set in the optical path for the fluorescence observation and is removed from the optical path for the bright-field observation.

The fluorescence cube 105 is a block that has the dichroic mirror 106 therein together with an optical filter such as an excitation filter or a barrier filter (not shown). The fluorescence cube 105 also has a mechanism for absorbing stray light. Note that the fluorescence cube 105 may be freely set in and removed from the optical path, and may be set in the optical path for the fluorescence observation and be removed from the optical path for the bright-field observation.

The dichroic mirror 106 is a type of a beam splitter that splits the fluorescence and the excitation light from each other, and splits the fluorescence and the excitation light from each other in accordance with the wavelengths. Note that the dichroic mirror 106 is a dichroic mirror having an optical characteristic that transmits the laser light from the laser 101 and reflects the fluorescence from sample S.

The collective lens 107 is a lens that is arranged in such a manner that the collective lens 107 can be freely set in and removed from the optical path between the dichroic mirror 106 and the objective 108 independently from other constituents and that has a positive power. The collective lens 107 is set in the optical path for the fluorescence observation and is removed from the optical path for the bright-field observation. The collective lens 107 constitutes together with the pupil projection lens 103 the pupil relay optical system projecting the pupil of the objective 108 onto the galvano mirror 102, and also constitutes together with a relay optical system 109, which will be described later, a pupil relay optical system projecting the pupil of the objective 108 onto the PMT 110, which will be described later.

The objective 108 is an infinite correction type objective that irradiates sample S with the laser light and converts the fluorescence from sample S into a parallel light flux. The objective 108 is attached to a revolver (not shown), and is used depending upon the purpose by switching from among objectives having different observation magnifications.

The microscope 100 includes the relay optical system 109 and the photomultiplier tube (PMT) 110 in the detection optical path of the fluorescence (fluorescence detection optical path) split from the laser light by the dichroic mirror 106.

The relay optical system 109 is arranged between the dichroic mirror 106 and the PMT 110, and constitutes, together with the collective lens 107, the pupil relay optical system projecting the pupil of the objective 108 onto the PMT 110. The PMT 110 is a photodetector that detects the fluorescence generated at sample S. The PMT 110 is a so-called non-Descanned detector (NDD) that is arranged at the pupil conjugate position of the objective.

The microscope 100 further includes a transmitted illumination unit (not shown) that illuminates sample S from below, a tube lens 111 that forms a bright-field observation image, a prism 112, an eyepiece lens 113, and a digital camera (not shown).

The transmitted illumination unit is an illumination unit for the bright-field observation, and includes for example a lamp light source, a condenser lens, etc. The transmitted illumination unit collects the illumination light into the pupil position of the condenser lens and evenly illuminates sample S from below. For the bright-field observation, in which the collective lens 107 and the mirror 104 have been removed from the optical path, the tube lens 111 is arranged at the position, on the bright-field detection optical path that has branched from both the laser optical path and the fluorescence detection optical path, on which light that has been transmitted through sample S and converted by the objective 108 into a parallel light flux is incident. The prism 112 is arranged on the image side of the tube lens 111, and guides, at a prescribed ratio, the light that has been converted by the tube lens 111 into a convergent light flux to the visual observation optical path in which the eyepiece lens 113 is arranged and to the camera optical path in which the digital camera is arranged.

Figure 3:
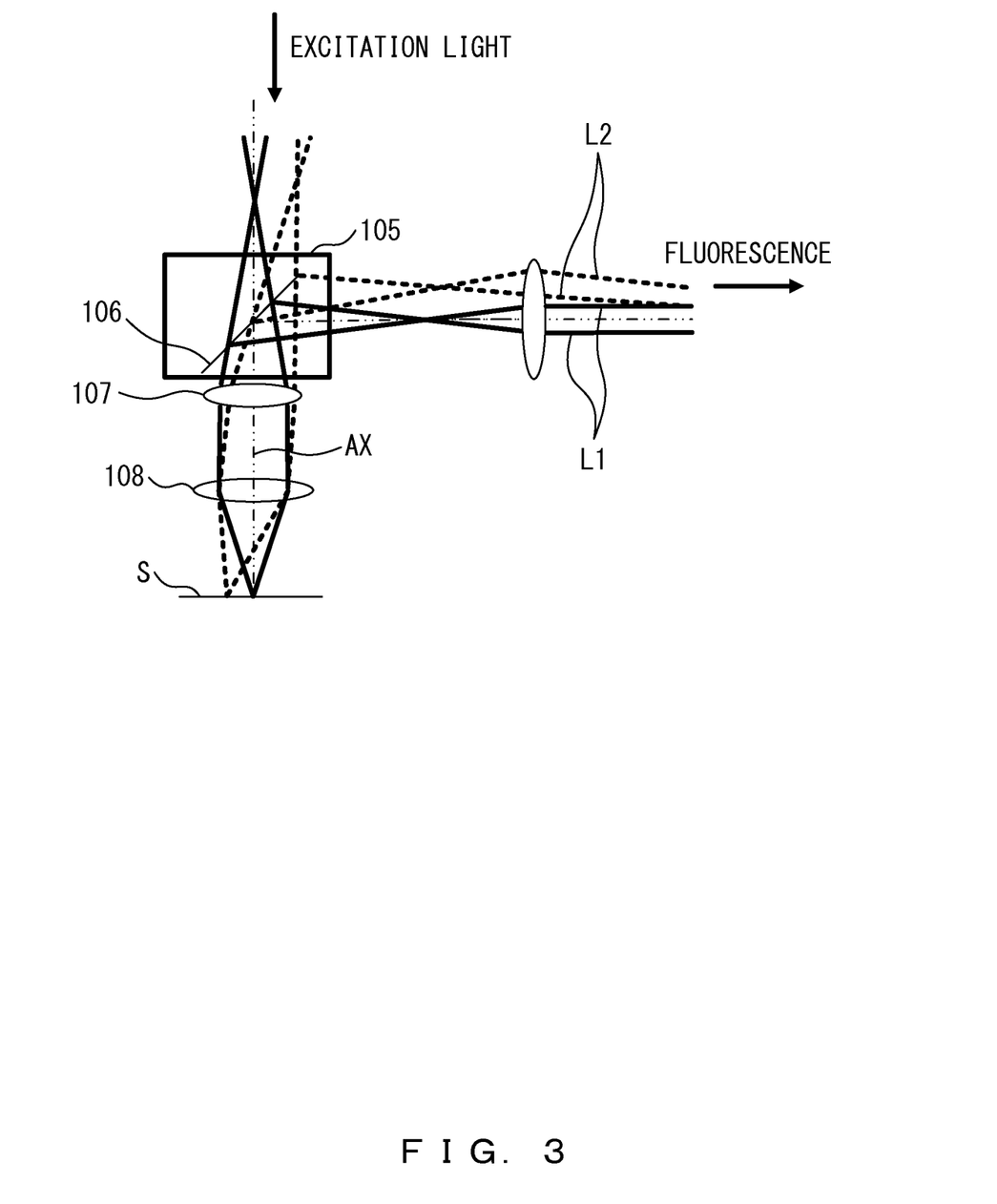
FIG. 3 shows on-axis light and off-axis light emitted from the objective to the dichroic mirror in the microscope according to embodiment 1 of the present invention.

As shown in FIG. 3, in the microscope 100, when the fluorescence observation is being performed, the fluorescence generated at sample S is converted into a convergent light flux by the positive power of the collective lens 107 after being converted into a parallel light flux by the objective 108 and before being incident on the dichroic mirror 106. Thereby, the fluorescence having a light flux diameter smaller than a case where the collective lens 107 does not exist is incident on the dichroic mirror 106. This makes it possible for the microscope 100 to suppress the occurrence of vignetting at the dichroic mirror 106. In particular, vignetting of off-axis light L2 that is incident on the dichroic mirror 106 at a position away from optical axis AX is reduced, making it possible to enlarge the capturing field of view from which is emitted fluorescence that can be captured, without increasing the diameter of the dichroic mirror 106.

Also, two-photon excitation microscopes realize observations into a deep portion of sample S; however, fluorescence tends to spread at sample S because the fluorescence generated at a deep portion of sample S tends to scatter in the sample. The microscope 100, which functions as a two-photon excitation microscope, can enlarge the capturing field of view on the sample surface due to the effects of the collective lens 107. This makes it possible to capture scattered fluorescence, leading to enhanced efficiency in detecting fluorescence.

Also, the microscope 100 can switch the observation methods between the fluorescence observation and the bright-field observation by setting the mirror 104 and the collective lens 107 in the optical path and removing them from the optical path. Thus, according to the microscope 100, it is possible to perform positioning of sample S and other settings in the bright-field observation before starting the fluorescence observation, making it possible to start the fluorescence observation without trouble. Further, because the collective lens 107 is removed from the optical path for the bright-field observation, in which the positioning of sample S and other settings are performed, light from the sample S is incident on the tube lens 111 as a parallel light flux. This makes it possible for the microscope 100 to form a bright-field observation image that is as excellent as in the conventional techniques for the bright-field observation while enlarging the capturing field of view for the fluorescence observation as described above.

Embodiment 2

Figure 4:
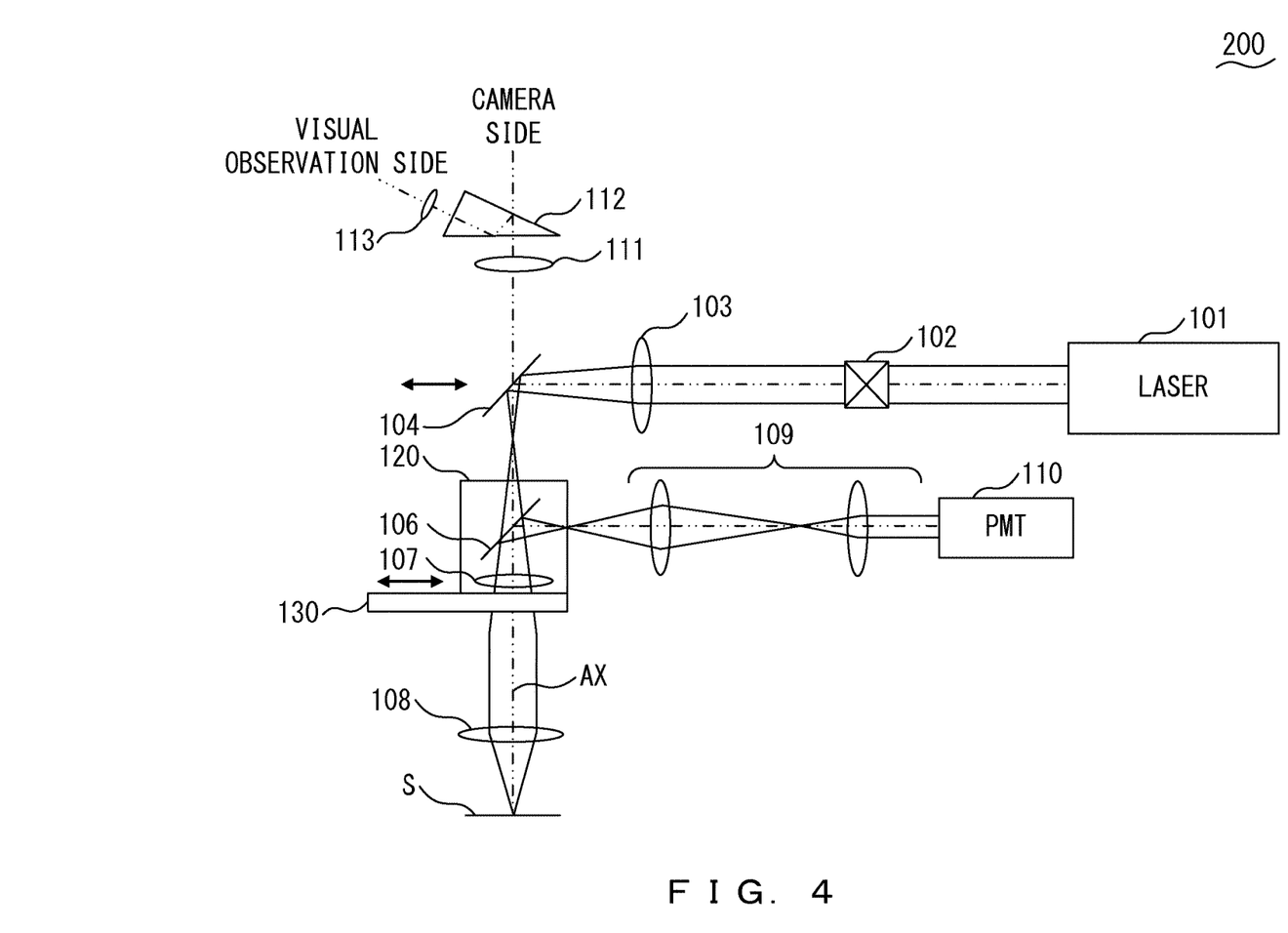
FIG. 4 exemplifies a configuration of a microscope according to embodiment 2 of the present invention.

FIG. 4 exemplifies a configuration of a microscope 200 according to the present embodiment. The microscope 200 is a microscope that switches the observation method between the bright-field observation and the fluorescence observation, and is similar to the microscope 100 according to embodiment 1 in that the microscope 200 functions as a two-photon excitation microscope for conducting the fluorescence observation.

The microscope 200 is different from the microscope 100 according to embodiment 1 in that the collective lens 107 is included in a fluorescence cube 120 in the microscope 200 and in that the microscope 200 includes a fluorescence cube turret 130 that switches the fluorescence cube arranged on optical axis AX. The microscope 200 is similar to the microscope 100 in the other components.

The fluorescence cube 120 is similar to the fluorescence cube 105 according to embodiment 1 in that the fluorescence cube 120 includes the dichroic mirror 106, an optical filter (an excitation filter and a barrier filter) (not shown), and a mechanism for absorbing stray light; however, the fluorescence cube 120 is different from the fluorescence cube 105 in that the fluorescence cube 120 has the collective lens 107 inside it. The collective lens 107 is arranged between the dichroic mirror 106 and the objective 108 in the fluorescence cube 120.

Figure 5:
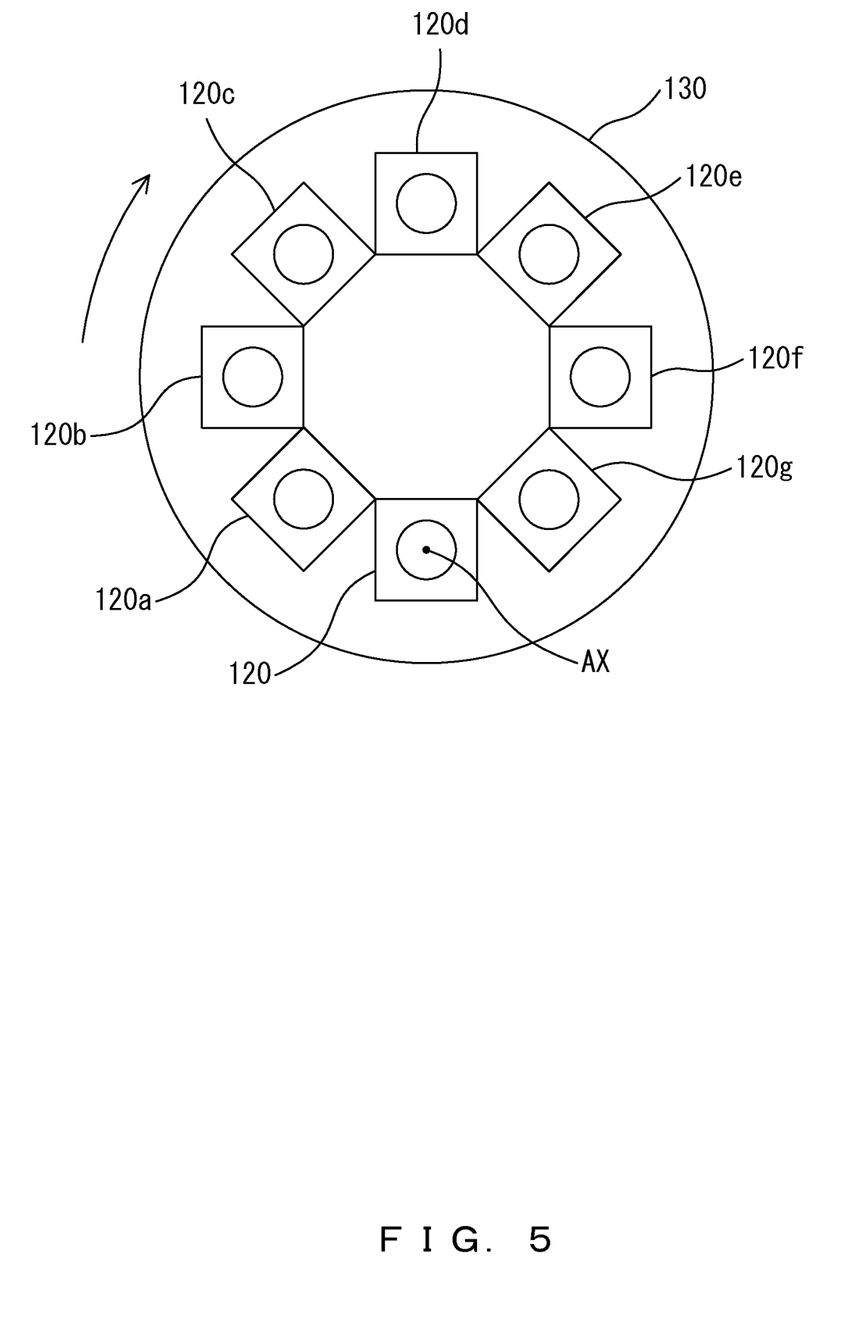
FIG. 5 exemplifies a configuration of a fluorescence cube turret included in the microscope according to embodiment 2 of the present invention.

As shown in FIG. 5, in the fluorescence cube turret 130, a plurality of fluorescence cubes (fluorescence cubes 120, 120a, 120b, 120c, 120d, 120e, 120f and 120g) are arranged. The fluorescence cube turret 130 is configured to switch the fluorescence cube that is on optical axis AX when the fluorescence cube turret 130 turns.

Also, the bright-field observation is performed by removing one of the fluorescence cubes or by arranging a cube not having both a collective lens 107 and a dichroic mirror 106 but having a hole, and is performed by turning the fluorescence cube turret 130 so that that the cube is set at the use position.

When the fluorescence cube 120 is set in or removed from the optical path by a turning of the fluorescence cube turret 130, the optical elements in the fluorescence cube 120 are also set in or removed from the optical path. In other words, in the microscope 200, the collective lens 107 and the dichroic mirror 106 are arranged in the fluorescence cube 120 in such a manner that the collective lens 107 and the dichroic mirror 106 can be freely set in and removed from the optical path, and the fluorescence cube turret 130 is a mechanism that coordinates the setting/removal of the collective lens 107 and the setting/removal of the dichroic mirror 106.

Similarly to the microscope 100 according to embodiment 1, it is possible according to the microscope 200 to enlarge the capturing field of view from which is emitted fluorescence that can be captured, without increasing the diameter of the dichroic mirror 106 by utilizing the effect of the collective lens 107. Also, because the collective lens 107 and the dichroic mirror 106 are simultaneously set or removed by the turning of the fluorescence cube turret 130, it is possible to simplify the process of switching the observation methods in comparison with the microscope 100 of embodiment 1, which sets and removes the collective lens 107 and the dichroic mirror 106 separately. The point at which the mirror 104 is set in or removed from the optical path for switching the observation methods is similar to the microscope 100.

Embodiment 3

Figure 6:
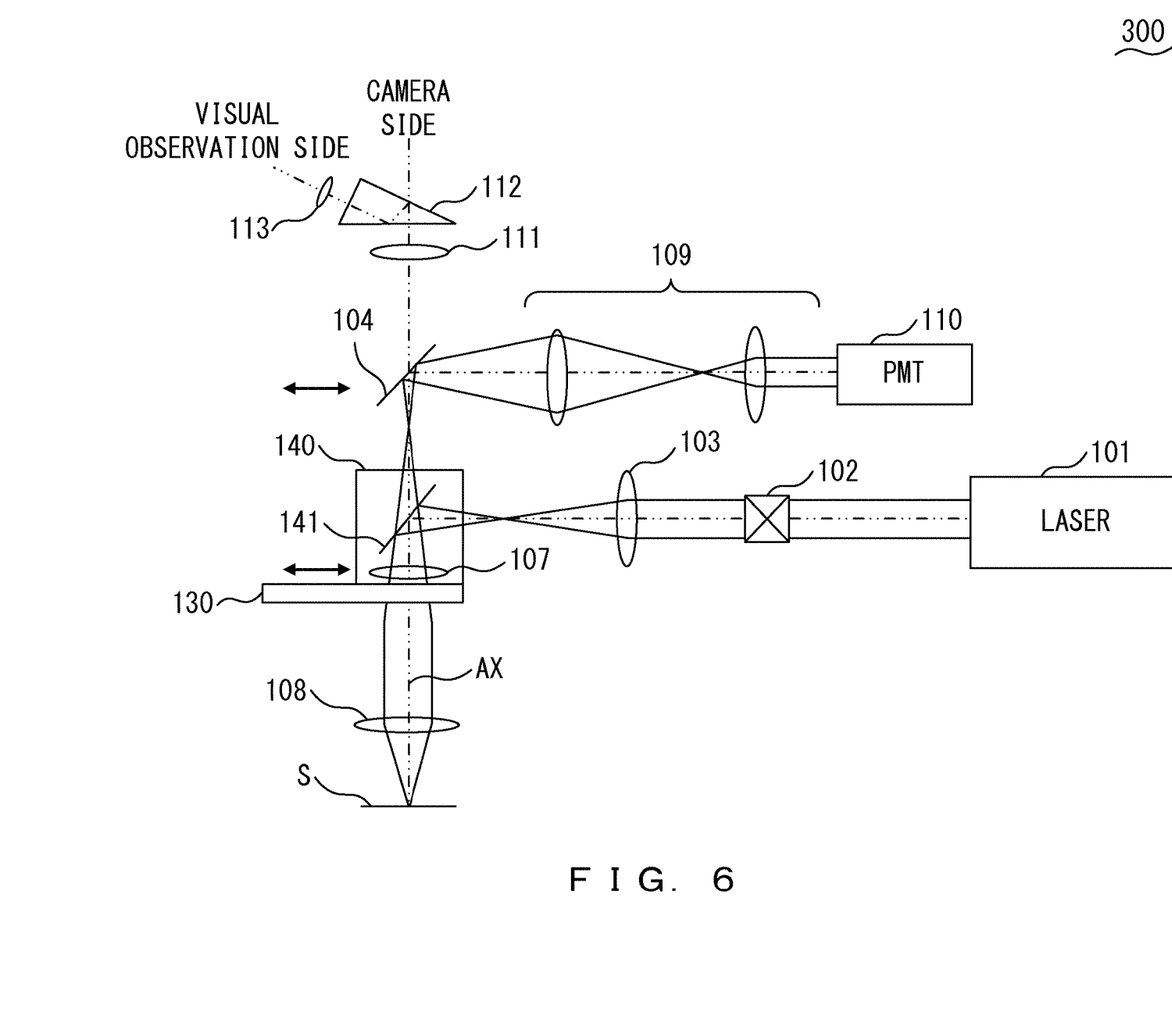
FIG. 6 exemplifies a configuration of a microscope according to embodiment 3 of the present invention.

FIG. 6 exemplifies a configuration of a microscope 300 according to the present embodiment. The microscope 300 is a microscope that switches the observation methods between the bright-field observation and the fluorescence observation, and is similar to the microscopes of embodiments 1 and 2 in that the microscope 300 functions as a two-photon excitation microscope when conducting the fluorescence observation.

The microscope 300 is different from the microscope 200 of embodiment 2 in that the microscope 300 has the laser 101 and the PMT 110 in positions reverse to those in the microscope 200 of embodiment 2. In other words, the microscope 300 is different from the microscope 200 in having the PMT 110 positioned at a level higher than the laser 101.

In order to realize the above positional relationship, the microscope 300 includes a fluorescence cube 140. The fluorescence cube 140 has therein the collective lens 107 having a positive power and a dichroic mirror 141 having an optical characteristic that reflects the laser light from the laser 101 and transmits the fluorescence from sample S. When the fluorescence observation is to be conducted, the fluorescence cube turret 130 is turned and the fluorescence cube 140 is set in the optical path as shown in FIG. 6.

Similarly to the microscopes of embodiments 1 and 2, the microscope 300 also makes it possible to enlarge the capturing field of view from which is emitted fluorescence that can be captured, without increasing the diameter of the dichroic mirror 106 by utilizing the effect of the collective lens 107. Also, similarly to the microscope of embodiment 2, because the collective lens 107 and the dichroic mirror 141 are simultaneously set or removed by the turning of the fluorescence cube turret 130, it is possible to simplify the process of switching the observation methods in comparison with the microscope 100 of embodiment 1, which sets and removes the collective lens 107 and the dichroic mirror 141 separately. It is desirable in view of the efficiency in the detection of fluorescence that the PMT 110 be disposed at a position lower than the laser 101, i.e., closer to sample S, similarly to the microscopes of embodiments 1 and 2.

FIG. 6 exemplifies a configuration in which the collective lens 107 is included in the fluorescence cube similarly to the microscope 200 of embodiment 2; however, it is also possible to dispose the collective lens 107 outside of the fluorescence cube similarly to the microscope 100 of embodiment 1. Thereby, it is possible to make the switching of the fluorescence cubes and the setting/removal of the collective lens 107 independent from each other. Accordingly, even when there are a plurality of fluorescence cubes employing different specifications to be used for the fluorescence observation, it is possible to use the collective lens 107 commonly for a plurality of such fluorescence cubes, without providing the collective lens 107 for each of the fluorescence cubes.

The embodiments described above are for facilitating the understanding of the invention, and the present invention is not limited to these embodiments. Various alterations and modifications are allowed for the microscopes described in the embodiments without departing from the spirit of the present invention, which is defined by the claims.

For example, while the embodiments described above exemplify a two-photon excitation microscope, the microscope of the present invention is not limited to a two-photon excitation microscope. The scope of the present invention includes for example any microscope that captures off-axis light such as any confocal microscope, and any fluorescence microscope that provides the planar illumination on sample S. Also, while the above embodiments exemplify upright microscopes, which observe sample S from above, the microscope of the present invention is not limited to an upright microscope and may be an inverted microscope.

Also, while the above embodiments exemplify a single lens as an example of the collective lens 107, the collective lens 107 is not limited to a single lens, and may include a plurality of lenses provided that the collective lens 107 has the positive power as a total lens. Also, while the above embodiments exemplify an example in which an intermediate image is formed by the collective lens 107 between the dichroic mirror 106 and the relay optical system 109, an intermediate image does not have to be formed by the collective lens 107 alone. For example, it is also possible to have an additional lens (referred to as a second collective lens) between the dichroic mirror 106 and the relay optical system 109 so that the collective lens 107 and the second collective lens form a intermediate image between the second collective lens and the relay optical system 109.

What is claimed is:

1. A microscope that switches an observation method between bright-field observation and fluorescence observation, comprising:
   an objective, to be used for the bright-field observation and the fluorescence observation, that irradiates a sample with excitation light and converts fluorescence from the sample into a parallel light flux;
   a beam splitter that splits the fluorescence and the excitation light from each other;
   a collective lens that is arranged in such a manner that the collective lens is freely set in and removed from an optical path between the beam splitter and the objective, that has positive power for collecting the parallel light flux from the objective, and that is set in the optical path for fluorescence observation relying on the objective and is removed from the optical path for bright-field observation relying on the objective;
   a scanner that scans the sample with the excitation light;
   a photodetector that detects the fluorescence generated at the sample; and
   a pupil relay optical system that projects a pupil of the objective into the photodetector and that includes the collective lens and an optical system arranged between the beam splitter and the photodetector.

2. The microscope according to claim 1, further comprising:
   a tube lens that forms a bright-field observation image, wherein the tube lens is arranged at a position, on an optical path that has branched from an optical path of the excitation light and an optical path of the fluorescence, on which light that has been converted by the objective into a parallel light flux is incident for bright-field observation.

3. The microscope according to claim 1, wherein:
   the beam splitter is arranged in such a manner that the beam splitter is freely set in and removed from an optical path, and
   the microscope further includes a mechanism that coordinates setting and removal of the collective lens and setting and removal of the beam splitter.

4. The microscope according to claim 3, wherein the mechanism is a fluorescence cube turret.

5. The microscope according claim 1, wherein the collective lens is arranged in such a manner that the collective lens is freely set in and removed from the optical path independently from a different component.

6. The microscope according to claim 1, wherein the beam splitter is a dichroic mirror.

7. A microscope that switches an observation method between bright-field observation and fluorescence observation, comprising:
   an objective, to be used for the bright-field observation and the fluorescence observation, that irradiates a sample with excitation light and converts fluorescence from the sample into a parallel light flux;
   a beam splitter that splits the fluorescence and the excitation light from each other;
   a collective lens that is arranged in such a manner that the collective lens is freely set in and removed from an optical path between the beam splitter and the objective, that has positive power for collecting the parallel light flux from the objective, and that is set in the optical path for fluorescence observation relying on the objective and is removed from the optical path for bright-field observation relying on the objective;
   a scanner that scans the sample with the excitation light;
   a photodetector that detects the fluorescence generated at the sample;
   a pupil relay optical system that projects a pupil of the objective into the photodetector and that includes the collective lens and an optical system arranged between the beam splitter and the photodetector;
   a tube lens that forms a bright-field observation image; and
   a mechanism that coordinates setting and removal of the collective lens and setting and removal of the beam splitter,
   wherein the tube lens is arranged at a position, on an optical path that has branched from an optical path of the excitation light and an optical path of the fluorescence, on which light that has been converted by the objective into a parallel light flux is incident for bright-field observation, and
   wherein the beam splitter is arranged in such a manner that the beam splitter is freely set in and removed from an optical path.

* * * * *